United States Patent [19]

Valyocsik

[11] Patent Number: 4,698,217

[45] Date of Patent: Oct. 6, 1987

[54] CRYSTALLINE SILICATE ZSM-58 AND PROCESS FOR ITS PREPARATION USING A METHYLTROPINIUM CATION

[75] Inventor: Ernest W. Valyocsik, Yardley, Pa.

[73] Assignee: Mobil Oil Corporation, New York, N.Y.

[21] Appl. No.: 861,789

[22] Filed: May 9, 1986

Related U.S. Application Data

[63] Continuation-in-part of Ser. No. 705,821, Feb. 26, 1985, abandoned.

[51] Int. Cl.[4] .............................................. C01B 33/28
[52] U.S. Cl. .................................. 423/328 C; 423/277; 423/326; 423/329; 423/330; 502/60; 502/62; 502/77; 502/202
[58] Field of Search ................ 423/328 T, 329; 502/77

[56] References Cited

U.S. PATENT DOCUMENTS

| | | | |
|---|---|---|---|
| 3,010,789 | 11/1961 | Milton | 423/328 C |
| 3,578,398 | 5/1971 | Jenkins | 423/328 T |
| 3,950,496 | 4/1976 | Ciric | 423/328 T |
| 4,411,902 | 10/1983 | Bernareggi | 424/265 |
| 4,432,983 | 2/1984 | Riley | 424/265 |
| 4,544,660 | 10/1985 | Hadley | 514/329 |
| 4,565,891 | 1/1986 | Correa | 564/298 |
| 4,592,902 | 6/1986 | Valyocsik | 423/328 |

FOREIGN PATENT DOCUMENTS

| | | | |
|---|---|---|---|
| 0040016 | 11/1981 | European Pat. Off. | 423/328 T |
| 0074651 | 3/1983 | European Pat. Off. | 423/328 T |

OTHER PUBLICATIONS

A. T. Bottini et al., "Stereochemistry of Tropane Quaternizations", *J. Org. Chem.*, 37(2), 324–6 (1972).
Gabor Fodor et al, "Stereochemistry of Tropane Quaternization", J. Amer. Chem. Soc., 93(2), 403–413 (1971).

*Primary Examiner*—John Doll
*Assistant Examiner*—Jackson Leeds
*Attorney, Agent, or Firm*—Alexander J. McKillop; Michael G. Gilman; Dennis P. Santini

[57] ABSTRACT

This invention relates to a new synthetic porous crystalline material, a method for its preparation and use thereof in catalytic conversion of organic compounds. The new crystalline material exhibits a distinctive X-ray diffraction pattern.

17 Claims, No Drawings

CRYSTALLINE SILICATE ZSM-58 AND PROCESS FOR ITS PREPARATION USING A METHYLTROPINIUM CATION

CROSS REFERENCE TO RELATED APPLICATION

This is a continuation-in-part of application Ser. No. 705,821, filed Feb. 26, 1985 and now abandoned.

BACKGROUND OF THE INVENTION

1. Field of the Invention

This invention relates to a novel synthetic porous crystalline material designated as "ZSM-58", to a method for its preparation and to its use in catalytic conversion of organic compounds.

2. Description of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminiosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), ZSM-38 (U.S. Pat. No. 4,046,859), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates or organosilicates of varying alumina and metal content.

SUMMARY OF THE INVENTION

The present invention is directed to a novel porous crystalline silicate material, designated as "ZSM-58", a method for its preparation, and the conversion of organic compounds contacted therewith.

The structure of ZSM-58 is distinguished from other crystalline silicates by a unique X-ray diffraction pattern. The typical X-ray diffraction pattern intensities for ZSM-58 are shown in Table 1, hereinafter.

The crystalline silicate ZSM-58 has a composition involving silica and alumina in the relationship

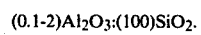

$(0.1-2)Al_2O_3:(100)SiO_2$.

In the as-synthesized form, ZSM-58 has a formula, on an anhydrous basis and in terms of moles of oxides per 100 moles of silica, as follows:

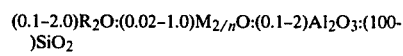

$(0.1-2.0)R_2O:(0.02-1.0)M_{2/n}O:(0.1-2)Al_2O_3:(100)SiO_2$ wherein M is an alkali or alkaline earth metal cation, n is the valence of M, and R is an organic cation.

ZSM-58 is thermally stable and exhibits molecular shape and selective properties as indicated by sorption tests.

DESCRIPTION OF SPECIFIC EMBODIMENTS

The original alkali or alkaline earth metal cations of the as synthesized ZSM-58 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-58 catalytically active, especially for certain hydrocarbon conversion reactions. These include hydrogen, rare earth metals of Groups IIA, IIIA, IVA, IB, IIB, IIIB, IVB and VIII of the Periodic Table of the Elements.

Typical ion exchange technique would be to contact the synthetic ZSM-58 with a salt of the desired replacing cation or cations. Examples of such slats include the halides, e.g. chlorides, nitrates and sulfates.

ZSM-58 crystals described and claimed herein have a typical X-ray diffraction pattern which distinguishes it from other crystalline materials. The intensities of that pattern are as follows:

TABLE 1

| Interplanar d-Spacing (A) | | Relative Intensity, I/Io |
|---|---|---|
| 13.70 | ±0.20 | W |
| 11.53 | ±0.20 | W-VS |
| 10.38 | ±0.20 | W |
| 7.82 | ±0.14 | W-VS |
| 6.93–6.79 | ±0.14 | W-VS |
| 6.19 | ±0.14 | W-VS |

TABLE 1-continued

| Interplanar d-Spacing (A) | | Relative Intensity, I/Io |
|---|---|---|
| 5.94 | ±0.12 | W-M |
| 5.77 | ±0.12 | VS |
| 5.22 | ±0.12 | W |
| 5.18 | ±0.10 | VS |
| 4.86 | ±0.09 | M-S |
| 4.72 | ±0.08 | S |
| 4.57 | ±0.08 | W |
| 4.51 | ±0.08 | S |
| 4.43 | ±0.08 | W |
| 4.19 | ±0.08 | W |
| 4.15 | ±0.08 | M |
| 4.00 | ±0.07 | W |
| 3.97 | ±0.07 | W |
| 3.89 | ±0.07 | W |
| 3.84 | ±0.07 | M |
| 3.81 | ±0.07 | W-M |
| 3.59 | ±0.06 | W |
| 3.46 | ±0.06 | W-M |
| 3.41 | ±0.06 | S-VS |
| 3.36 | ±0.06 | S-VS |
| 3.32 | ±0.06 | M-S |
| 3.29 | ±0.05 | W |
| 3.17 | ±0.05 | W-M |
| 3.07 | ±0.05 | W-M |
| 3.05 | ±0.05 | W-M |
| 3.01 | ±0.05 | W-M |
| 2.88 | ±0.05 | W |
| 2.85 | ±0.05 | W |
| 2.75 | ±0.05 | W |
| 2.67 | ±0.04 | W |
| 2.60 | ±0.04 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Table 1, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that this X-ray diffraction pattern is characteristic of all the species of ZSM-58 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment. Multiplets may be observed in the typical X-ray pattern for ZSM-58 at d-spacing values of 6.93–6.79±0.14, 4.86±0.09, 3.41±0.06, 3.07±0.05 and 3.01±0.05 Angstroms.

The crystalline silicate of the present invention can be used either in the alkali or alkaline earth metal form, e.g. the sodium or potassium form; the ammonium form; the hydrogen form or another univalent or multivalent cationic form. When used as a catalyst, ZSM-58 will be subjected to thermal treatment to remove part or all of any organic constituent.

The crystalline silicate can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be formed. Such component can be exchanged into the composition to the extent aluminum is in the structure, impregnated therein or intimately physically admixed therewith. Such component can be impregnated in or on to it such as for example, by, in the case of platinum, treating the ZSM-58 with a solution containing a platinum metal-containing ion. Thus, suitable platinum compounds include chloroplatinic acid, platinous chloride and various compounds containing the platinum amine complex.

The above crystalline silicate, especially in its metal, hydrogen and ammonium forms can be beneficially converted to another form by thermal treatment. This thermal treatment is generally performed by heating one of these forms at a temperature of at least 370° C. at least 1 minute and generally not longer than 20 hours. While atmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

The new silicate, when employed either as an adsorbent or as a catalyst in an organic compound conversion process should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-58 in a vacuum, but a longer time is required to obtain a sufficient amount of dehydration.

The new crystalline silicate can be prepared from a reaction mixture containing sources of an alkali or alkaline earth metal (M) cation, an oxide of aluminum, an oxide of silicon, an organic cation (R) of a methyltropinium salt, e.g. halide, hydroxide, sulfate, etc., and water, said reaction mixture having a composition, in terms of mole ratios of oxides, within the following ranges:

| Reactants | Useful | Preferred |
|---|---|---|
| $SiO_2/Al_2O_3$ | 50–1000 | 70–500 |
| $H_2O/SiO_2$ | 5–200 | 10–100 |
| $OH^-/SiO_2$ | 0–2.0 | 0.10–1.0 |
| $M/SiO_2$ | 0.01–3.0 | 0.10–1.0 |
| $R/SiO_2$ | 0.01–2.0 | 0.10–0.50 | wherein R and M are as above defined.

Crystallization of the new ZSM-58 can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered. The reaction mixture can be prepared utilizing materials which supply the appropriate oxides. Such materials may include sodium silicate, silica hydrosol, silica gel, silicic acid, sodium hydroxide, a source of aluminum, and the methyltropinium salt directing agent. The methyltropinium salt may be synthesized by selective methylation of 3-tropanol at the bridgehead nitrogen. This salt has the following formula:

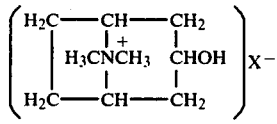

wherein X is an anion, such as, for example, a halide (e.g. iodide, chloride or bromide), nitrate, hydroxide, sulfate, bisulfate, perchlorate, etc.

It should be realized that the reaction mixture oxides can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the ZSM-58 crystals is facilitated by the presence of at least 0.01 percent, preferably 0.10 percent and still more preferably 1 percent, seed crystals (based on total weight) of crystalline product.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In general, organic compounds such as, for example, those selected from the group consisting of hydrocarbons, alcohols and ethers, are converted to conversion products such as, for example, aromatics and lower molecular weight hydrocarbons, over catalyst comprising the crystalline silicate ZSM-58 hereof by contact under organic compound conversion conditions including a temperature of from about 100° C. to about 800° C., a pressure of from about 0.1 atmosphere (bar) to about 200 atmospheres, a weight hourly space velocity of from about 0.08 hr$^{-1}$ to about 2000 hr$^{-1}$ and a hydrogen/feedstock organic compound mole ratio of from 0 (no added hydrogen) to about 100.

Such conversion processes include, as non-limiting examples, cracking hydrocarbons to lower molecular weight hydrocarbons with reaction including a temperature of from about 300° C. to about 800° C., a pressure of from about 0.1 atmosphere (bar) to about 35 atmospheres and a weight hourly space velocity of from about 0.1 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components to product enriched in p-xylene with reaction conditions including a temperature from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene to product comprising benzene and xylenes with reaction conditions including a temperature of from about 200° C. to about 760° C., a pressure of from about atmospheric to about 60 atmospheres and a weight hourly space velocity of from about 0.08 to about 20; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new ZSM-58 crystal, i.e. combined therewith, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the monotrillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the ZSM-58 crystal can be composited with a porous matrix material such as silica-alumina, silica-magnesia, silica zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for cyclohexane and/or n-hexane, they were determined as follows:

A weighed sample of the calcined adsorbant was contacted with the desired pure adsorbate vapor in an adsorption chamber, evacuated to less than 1mm and contacted with 80 mm Hg of n-hexane or cyclohexane vapor, pressures less than the vapor-liquid equlibrium pressure of the respective adsorbate at 90° C. The pressure was kept constant (within about ±0.5 mm) by addition of absorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of clacined adsorbant.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant =0.016 sec$^{\pm 1}$). The Alphs Test is described in U.S. Pat. No. 3,354,078 and in the Journal of Catalysis, Vol. IV, pp. 522–529 (Aug. 1965), each incorporated herein as to that description. It is noted that intrinsic rate constants for many acid-catalyzed reactions are proportional to the Alpha Value for a particular crystalline silicate catalyst, i.e. the rates for toluene disproportionation, xylene isomerization, alkene conversion and methanol conversion (see "The Active Site of Acidic Aluminosilicate Catalysts," *Nature*, Vol. 309, No. 5969, pp. 589–591, 14 June 1984).

EXAMPLES 1–6

Six separate synthesis reaction mixtures were prepared with compositions indicated in Table 2. The mixtures were prepared with silica sol (30 percent $SiO_2$), $NaAlO_2$, NaOH, a methyltropinium salt, i.e. iodide, and water. The mixtures were maintained at 160° C. for 4 days in a stainless steel, stirred (400 rpm) autoclave at autogenous pressure. Solids were separated from any unreacted components by filtration and then water washed, followed by drying at 110° C. The product crystals were analyzed by X-ray diffraction and chemical analysis. The product of Example 1 was found to be crystalline ZSM-58 with a trace of unidentified second component impurity. The products from Examples 2–6 proved to be 100 percent crystalline ZSM-58.

The X-ray diffraction pattern of the Example 4 crystals, after calcination at 538° C. for 17 hours in air, is set forth as illustration in Table 3. Other properties of each crystalline product are presented in Table 4. In the latter table, compositions are calculated on the basis of 100 ($SiO_2$ ±$AlO_2^-$) tetrahedrea. The as-synthesized ZSM-58 from these examples contains from 3.8 to 5.0 methyltropinium cations per 100 tetrahedra.

TABLE 2

| | Mixture Composition (mole ratios) | | | | |
|---|---|---|---|---|---|
| Example | $SiO_2$ $Al_2O_3$ | $H_2O$ $SiO_2$ | $OH^-$ $SiO_2$ | $Na^+$ $SiO_2$ | $R^*$ $SiO_2$ |
| 1 | 300 | 40 | 0.30 | 0.31 | 0.25 |
| 2 | 200 | 40 | 0.30 | 0.31 | 0.25 |
| 3 | 90 | 40 | 0.40 | 0.42 | 0.25 |
| 4 | 90 | 40 | 0.30 | 0.32 | 0.25 |
| 5 | 90 | 40 | 0.30 | 0.32 | 0.25 |
| 6 | 70 | 40 | 0.30 | 0.33 | 0.25 |

*R = methyltropinium cation.

TABLE 3

| d (A) | Observed 2 Theta | Relative Intensity |
|---|---|---|
| 13.57425 | 6.511 | 7.4 |
| 11.44933 | 7.721 | 51.2 |
| 10.29541 | 8.588 | 4.1 |
| 7.76959 | 11.389 | 53.6 |
| 6.89736 | 12.834 | 60.1 |
| 6.84556 | 12.932 | 33.0 |
| 6.15999 | 14.378 | 57.8 |
| 5.91115 | 14.987 | 19.5 |
| 5.74071 | 15.435 | 85.8 |
| 5.16339 | 17.173 | 100.0 |
| 4.84326 | 18.317 | 51.9 |
| 4.70389 | 18.865 | 56.0 |
| 4.52632 | 19.612 | 20.3 |
| 4.49392 | 19.755 | 51.7 |
| 4.41905 | 20.093 | 4.7 |
| 4.13559 | 21.486 | 26.0 |
| 3.98517 | 22.307 | 11.8 |
| 3.96826 | 22.404 | 8.9 |
| 3.87191 | 22.969 | 17.1 |
| 3.82281 | 23.268 | 30.6 |
| 3.80712 | 23.365 | 25.6 |
| 3.57841 | 24.882 | 16.2 |
| 3.44668 | 25.849 | 35.2 |
| 3.38811 | 26.303 | 96.5 |
| 3.35769 | 26.546 | 86.7 |
| 3.34862 | 26.619 | 80.8 |
| 3.30859 | 26.947 | 66.2 |
| 3.28346 | 27.158 | 9.1 |
| 3.16039 | 28.237 | 23.3 |
| 3.06246 | 29.159 | 26.8 |
| 3.06070 | 29.176 | 31.2 |
| 3.03737 | 29.406 | 22.7 |
| 2.99654 | 29.816 | 25.2 |
| 2.98814 | 29.901 | 21.2 |
| 2.87045 | 31.158 | 4.1 |

TABLE 3-continued

| d (A) | Observed 2 Theta | Relative Intensity |
|---|---|---|
| 2.84237 | 31.473 | 5.1 |
| 2.66429 | 33.638 | 5.5 |
| 2.58922 | 34.643 | 4.8 |
| 2.50349 | 35.869 | 4.3 |
| 2.48809 | 36.099 | 6.3 |
| 2.43821 | 36.863 | 9.0 |
| 2.42105 | 37.134 | 14.9 |
| 2.39052 | 37.626 | 5.8 |
| 2.35412 | 38.230 | 2.8 |
| 2.33296 | 38.591 | 4.3 |
| 2.30029 | 39.161 | 16.7 |
| 2.23686 | 40.319 | 2.4 |
| 2.23188 | 40.413 | 1.9 |
| 2.21126 | 40.807 | 3.2 |
| 2.16400 | 41.739 | 1.7 |
| 2.11106 | 42.836 | 1.4 |
| 2.07314 | 43.660 | 3.0 |
| 2.03910 | 44.427 | 0.3 |
| 1.97783 | 45.880 | 11.4 |
| 1.95022 | 46.568 | 4.4 |
| 1.93214 | 47.030 | 3.9 |
| 1.91503 | 47.476 | 3.7 |
| 1.83810 | 49.594 | 6.4 |
| 1.83554 | 49.667 | 5.5 |

TABLE 4

| Ex. ample | Moles C Mole N | Moles per Mole $Al_2O_3$ | | | COMPOSITION Al 100 $T_d$ | $Na^+$ 100 $T_d$ | $N^+$ 100 $T_d$ | R 100 $T_d$ |
|---|---|---|---|---|---|---|---|---|
| | | $N_2O$ | $Na_2O$ | $SiO_2$ | | | | |
| 1 | 9.5 | 4.09 | 0.85 | 223 | 0.89 | 0.76 | 3.6 | 3.8 |
| 2 | 11.2 | 2.43 | 0.74 | 140 | 1.4 | 1.0 | 3.4 | 4.2 |
| 3 | 9.6 | 1.85 | 0.13 | 83 | 2.4 | 0.30 | 4.4 | 4.7 |
| 4 | 10.2 | 1.69 | 0.12 | 78 | 2.5 | 0.30 | 4.2 | 4.8 |
| 5 | 10.8 | 1.77 | 0.25 | 85 | 2.3 | 0.58 | 4.1 | 4.9 |
| 6 | 9.6 | 1.50 | 0.10 | 62 | 3.1 | 0.30 | 4.7 | 5.0 |

EXAMPLE 7

A sample of the Example 4 product crystals, having been calcined in nitrogen for 4 hours at 500° C., ammonium exchanged and then converted to the hydrogen form, was subjected to the sorption test. Significant n-hexane, i.e. 8 weight percent at 90° C., was sorbed while only minimal cyclohexane (about 1 weight percent at 90° C.) sorbed at 80 torr hexane partial pressure. This indicates molecular shape selectivity for the ZSM-58 of this invention.

EXAMPLE 8

The sample of Example 4 product used for sorption evaluation was evaluated in the Alpha Test. Its Alpha Value proved to be 13 at 538° C.

What is claimed is:

1. A synthetic porous crystalline material being characterized by (1) an X-ray diffraction pattern exhibiting values substantially as set forth in TABLE 1 of the specification and (2) a composition comprising silica and alumina in the relationship $(0.1-2)Al_2O_3:(100)SiO_2$.

2. The crystalline material of claim 1 in the as-synthesized form having a composition, on an anhydrous basis and in terms of moles of oxides per 100 moles of silica, expressed by the formula:

$(0.1-2.0)R_2O:(0.02-1.0)M_{2/n}O:(0.1-2)Al_2O_3:(100)SiO_2$ wherein M is an alkali or alkaline earth metal cation, n is the valence of M, and R is a methyltropinium cation.

3. The crystalline material comprising the crystalline material of claim 2 having original cations replaced, at least in part, with a cation or a mixture of cations selected from the group consisting of hydrogen and hydrogen precursors, rare earth metals, and metals of Groups IIA, IIIA, IVA, IB, IIB, IIIB, IVB, and VIII of the Periodic Table of the Elements.

4. The crystalline material resulting from thermal treatment of the crystalline material of claim 2 at a temperature of from about 370° C. to about 925° C.

5. The crystalline material resulting from thermal treatment of the crystalline material of claim 3 at a temperature of from about 370° C. to about 925° C.

6. A method for preparing the synthetic crystalline material of claim 2, said method comprising preparing a reaction mixture capable of forming said material upon crystallization, said reaction mixture containing sufficient amounts of an alkali metal or alkaline earth metal oxide, an oxide of silicon, an oxide of aluminum, water and methyltropinium salt directing agent of the formula:

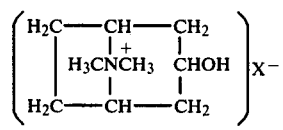

wherein X is an anion, and maintaining said reaction mixture under sufficient crystallization conditions until crystals of said material are formed.

7. The method of claim 6 wherein said reaction mixture has a composition in terms of mole ratios within the following ranges:
$SiO_2/Al_2O_3 = 50$ to $1000$
$H_2O/SiO_2 = 5$ to $200$
$OH^-/SiO_2 = 0$ to $2.0$
$M/SiO_2 = 0.01$ to $3.0$
$R/SiO_2 = 0.01$ to $2.0$
wherein M represents alkali metal or alkaline earth metal cations and R represents methyltropinium cations.

8. The method of claim 7 wherein said reaction mixture has a composition in terms of mole ratios within the following ranges:
$SiO_2/Al_2O_3 = 70$ to $500$
$H_2O/SiO_2 = 10$ to $100$
$OH^-/SiO_2 = 0.10$ to $1.0$
$M/SiO_2 = 0.10$ to $1.0$
$R/SiO_2 = 0.10$ to $0.50$.

9. The method of claim 6, wherein said reaction mixture further comprises a sufficient amount of crystal formation enhancing seed crystals of crystalline product.

10. A reaction mixture capable of forming the crystalline material of claim 2 upon crystallization, said reaction mixture containing sufficient amounts of an alkali metal or alkaline earth metal oxide, an oxide of silicon, an oxide of aluminum, water and a methyltropinium salt directing aganet of the formula:

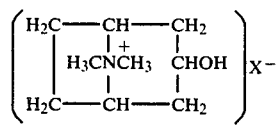

wherein X is an anion.

11. The reaction mixture of claim 10 having a composition in terms of mole ratios within the following ranges:

$SiO_2/Al_2O_3 = 50$ to $1000$
$H_2O/SiO_2 = 5$ to $200$
$OH^-/SiO_2 = 0$ to $2.0$
$M/SiO_2 = 0.01$ to $3.0$
$R/SiO_2 = 0.01$ to $2.0$ wherein M represents alkali metal or alkaline earth metal cations and R represents methyltropinium cations.

12. The reaction mixture of claim 11 having a composition in terms of mole ratios within the following ranges:

$SiO_2/Al_2O_3 = 70$ to $500$
$H_2O/SiO_3 = 10$ to $100$
$OH^-/SiO_2 = 0.10$ to $1.0$
$M/SiO_2 = 0.10$ to $1.0$
$R/SiO_2 = 0.10$ to $0.50$.

13. The reaction mixture of claim 10 having a sufficient amount of crystal formation enhancing seed crystals of crystalline product.

14. The crystalline material of claim 3 wherein said replacing cations comprises hydrogen or a hydrogen precursor.

15. The crystalline material of claim 3 wherein said replacing cations comprise metals selected from the group consisting of rare earth metals of Groups IIA, IIIA, IVA, IB, IIB, IIIB, IVB, VIB and VIII of the Periodic Table of the Elements.

16. A composition comprising the crystalline material of claim 1 and a matrix.

17. The composition of claim 16 wherein said matrix comprises alumina.

* * * * *